United States Patent [19]

Hevey

[11] 4,234,316

[45] Nov. 18, 1980

[54] DEVICE FOR DELIVERING MEASURED QUANTITIES OF REAGENTS INTO ASSAY MEDIUM

[75] Inventor: Richard C. Hevey, Rockport, Me.

[73] Assignee: FMC Corporation, Philadelphia, Pa.

[21] Appl. No.: 25,997

[22] Filed: Apr. 2, 1979

[51] Int. Cl.³ .......................................... G01N 33/50
[52] U.S. Cl. ............................. 23/230 R; 23/230 B; 23/901; 23/902; 23/905; 23/915; 23/923; 252/408; 422/50; 422/57; 422/58; 422/68; 435/14; 435/300; 435/810
[58] Field of Search ............. 23/230 R, 230 B; 424/1; 422/50, 57, 58, 68; 252/408

[56] References Cited

U.S. PATENT DOCUMENTS

| | | | |
|---|---|---|---|
| 3,935,303 | 1/1976 | Khromov | 424/14 |
| 3,975,162 | 8/1976 | Renn | 424/12 X |
| 4,029,758 | 6/1977 | Mlodzeniec | 424/19 |
| 4,046,513 | 9/1977 | Johnson | 427/2 X |
| 4,062,652 | 12/1977 | Birgitta | 422/61 |
| 4,135,884 | 1/1979 | Shen | 422/58 X |

FOREIGN PATENT DOCUMENTS 750849 11/1970 Belgium.

OTHER PUBLICATIONS

Chemical Abstracts, 84: 71192j (1976).

Primary Examiner—Sidney Marantz
Attorney, Agent, or Firm—Eugene G. Horsky; Charles H. Johnson

[57] ABSTRACT

Device for delivering precise measured quantities of a plurality of reagents with each reagent being incorporated in a device and each being water soluble. The device has a water impervious support secured to one or more faces of which are discrete and separate elements each containing water soluble or dispersible binder and dispersed therein a water soluble or dispersible reagent. The reagent of each element in the device is reactive with at least one constituent in an assay medium or with at least one other reagent on the device. The device is used by contacting it with the assay medium until the elements dissolve completely.

11 Claims, 4 Drawing Figures

DEVICE FOR DELIVERING MEASURED QUANTITIES OF REAGENTS INTO ASSAY MEDIUM

This invention relates to an assay device and method for delivering measured quantities of two or more water-soluble or water-dispersible reagents to an aqueous assay medium.

A variety of devices or tools have been developed for the delivery of reagents to an assay medium. In the chemical analysis of liquids such as water, foodstuffs, and biological fluids, the quantitative, accurate delivery has been effected by pipetting devices which can be operated either manually or automatically. Devices such as manually operated micropipettes are capable of delivering microliter quantities of a reagent whereas automatic pipetting devices can be utilized for delivering similar volumes, requiring only the filling of a reservoir.

Various other devices to facilitate liquid analysis are known. Such devices have often included a reagent for a substance under analysis (the analyte) which reagent upon contacting a liquid sample containing the analyte effects formation of a colored material or another detectable change in response to the presence of the analyte. Among such devices are, for example, pH test strips and similar indicators where a paper or other highly absorbent insoluble carrier is impregnated with a material, chemically reactive, that responds to contact with the liquid containing, for example, hydrogen ion or other analyte, and either generates color or changes color. Such reagents are usually mixed with a solid water resistant carrier, and analyte together with water or other solvent or liquid reaction medium must impregnate the carrier for a reaction to occur. However, reagents in insoluble carriers cannot be readily extracted and diffused into water or other solvent or liquid medium but instead tend to form a mixture with most of the reagents remaining in the insoluble carriers, making precise control and measurement of the quantity of reagent introduced into the medium impractical.

Much developmental work has been directed towards providing devices useful in diagnostic chemical analysis, where testing of biological liquids such as blood, plasma, urine, etc., must produce precise quantitative results, rapidly and accurately.

"Wet" chemical techniques have enjoyed broad acceptance in analytical chemistry and clinical chemistry. Particularly outstanding has been the introduction of automatic analyzers facilitating rapid quantitative results. However, such analyzers are often expensive and cumbersome, usually requiring a skilled person for operation and maintenance.

As indicated above, various integral elements for non-solution or "dry" chemical analysis have been proposed as an alternative to solution chemistry for qualitative or semi-quantitative purposes. One variety of such a device for drug dispensing is described in U.S. Pat. No. 3,935,303, which uses polyacrylamide as a binder in an unsupported fashion to deliver medication to the eye, i.e., an opthalmological medicinal film. Upon contact with the eye of the film containing a single opthalmologically active ingredient or upon introduction of the film into the conjunctival cavity, it is quickly dissolved and assimilated. Such a device is limited to polymers of acrylamide or copolymers of acrylamide which can be assimilated by tissue or are at least biologically compatible with eye tissues.

In U.S. Pat. No. 3,975,162 there is described a device for applying a measured quantity of water-soluble or water-dispersible reagent to a water-containing solid medium for use in molecular diffusion or affinity separation procedures. The device, consisting of a water-insoluble film-forming solid organic polymeric binder containing a measured quantity of reagent, is used by placing it in face-to-face contact with a water-containing solid medium whereupon the reagent and binder diffuse completely into said medium. However, there is no mention of a device for quantitatively delivering two or more physically separated and distinct reagents simultaneously to a medium.

U.S. Pat. No. 4,046,513 provides a test device comprising reactants (e.g., reagents, enzymes, etc.) incorporated in water-insoluble carrier matrix such as cross-linked polyacrylamide, polystyrene, or cellulose acetate; when the device is wetted with a test sample, the reactants and the test constituent react to produce a detectable response on the device. The reactants are positioned separately from each other in the matrix in discrete, non-contacting areas and react on the surface of the test device, the latter requirement necessitating that the reactants lie on the same surface or plane of the device; and because of the water-insolubility of the carrier matrix, not all of the reactant dissolves in the water in which the matrix is immersed but instead an equilibrium mixture is formed, with most of the reactants remaining within the matrix.

The present invention provides a device and method which facilitates precise quantitative introduction of reagents into an aqueous assay medium for the quantitative determination of an analyte. The device of the present invention comprises a water-impervious solid support member chemically inert to, i.e., non-reactive with the reagents and to the material which is to be assayed, the support member carrying secured to one or more faces two or more discrete and separate elements consisting essentially of carrier organic binder which is soluble in water and dispersed in each binder a measured quantity of water-soluble or water-dispersible reagent, the reagent in each element being reactive with at least one constituent in the assay medium and/or reactive with the reagent in other elements, the elements on the support member of the device being of a size and shape adapted to allow contact, while still on the device, with a liquid water medium to permit the reagent and binder to dissolve or disperse completely into the liquid medium. Included among the binders which are soluble in water are those which form colloidal solutions or dispersions as well as those which form true solutions.

In one embodiment, the elements may all be secured to a single face of the support member, each element being separated from the others by a space; in another embodiment, the elements may be separated from each other by being in contact with opposite faces of a physical separator or barrier. For example, two elements may be secured to opposite faces of a water-impervious solid support member in the form of a sheet, the latter serving both as a support member and as a physical separator preventing contact between the two elements. In another example of this embodiment, two or more elements are overlaid on each other to form a stack, the bottommost one of which is secured to the water-impervious support member, each element being separated from adjacent elements in the stack by a separator in the form of a film or layer of water-soluble organic binder free from reagent, or by a film or layer of water-impervious material.

The binders which can be used in the present invention include various polymeric materials such as dextran, water-soluble polyacrylamide, polyacrylic acid and water-soluble metal salts thereof, water-soluble polyvinyl alcohol, polyethylene glycol, polyethylene oxide, polyvinylpyrrolidone, clarified guar gum, water-soluble carboxymethyl cellulose, water-soluble hydroxyethyl cellulose, water-soluble methyl cellulose, algin, carrageenan, xanthan gum, starch, water-soluble copolymers of maleic anhydride with various vinyl monomers as described, for example, in U.S. Pat. No. 2,047,398 particularly copolymers of maleic anhydride with vinyl ether, or vinyl ester, or their corresponding salts. There can also be present along with the binder conventional humectants or surface active agents (dispersing agents) to maintain the flexibility of the binder and to facilitate or accelerate its dispersion or dissolution in water. In addition, binders of non-polymeric, relatively low molecular weight molecules can be used including sorbitol, potassium sodium tartrate, mannose, and sucrose. Binders composed of mixtures of two or more different materials can also be used.

The element containing binder and reagent may be of any desired thickness but is preferably from 0.01 to 2 mm. thick. The insoluble solid support member can be made of glass or of such plastics as polyester, polystyrene, cellulose acetate, superpolyamide and the like of varying thickness. The thickness of the support member is usually kept to a minimum in order to minimize cost while at the same time providing the desired mechanical reinforcement or strength. The extent of bonding or securing of the reagent binder film to the support member is not critical, sufficient bonding usually being provided if the binder is formed in situ on the surface of the support member from a solution or a melt.

The reagents which can be incorporated in the binder can be any of the water-soluble or water-dispersible materials which are commonly employed in analytical procedures, such as enzymes, enzyme substrates, antibodies, antigens, haptens, inorganic and organic reagents, buffers, salts, and the like, as well as radioactively tagged or fluorescent reagents of the foregoing types including nonisotopic tags such as enzymes, cofactors, luminescent agents, and the like.

The relative proportions of reagent and of water-soluble polymeric binder in the device can be varied widely depending upon the size or amount of the measured quantity which is desired and is a matter of convenience. Usually it is most convenient to employ a device in which the water-soluble binder amounts to about 2 to 95% by weight of the element while the reagent constitutes the remainder. While there may be included in a single element two or more reagents which are compatible, i.e., non-reactive, with each other, those which are reactive (i.e., which react with each other or which cause decomposition of one or the other over a period of time) must be present only in discrete and separate elements.

The reagents can be incorporated in the element binder in a variety of ways. The reagent can be mixed with the binder while the latter is in a molten form or in the form of a solution in a volatile solvent, after which the mixture is formed into a film of the desired thickness and allowed to dry or cool in order to solidify it. The element of water-soluble binder can also be formed separately, from a solution of the binder or from a melt, after which a solution or dispersion of the reagent in a suitable liquid vehicle can be applied to the surface of the element, allowed to diffuse into the element and the film dried. In some cases, the reagent in dry, finely-divided particulate form can be spread on the surface of the binder element after which the latter is melted and resolidified. While forced air drying can usually be employed in forming the film and/or incorporating the reagent in the film, vacuum or freeze-drying can also be employed in the case of heat-sensitive materials.

The size and configuration of the device of the present invention is a matter of choice depending upon the nature of the assay procedure being carried out. Devices may be, for example, relatively stiff or rigid water-insoluble support members in strip form onto which discrete reagent-binder spots are placed, or propeller shaped support members containing discrete spaced-apart elements containing different reagents on each surface of the propeller blades. The support member onto which the reagent and binder are placed may be of any desired shape, including annular or perforated. Preferably the support member is stiff and elongated, having one end portion constructed and arranged to act as a handle or gripping portion to be grasped by the fingers of the user and another end portion, adapted to be contacted with an aqueous test liquid, to which the discrete binder elements containing the reagents are secured. In use, such a device is grasped by the fingers near one end and the other end is contacted with a test liquid until all of the reactants along with the binders have dissolved. Dissolution can be accelerated in most cases by stirring the liquid with the support member, a step which also ensures homogeneous distribution of the reactants throughout the test liquid.

The devices of the present invention can be employed to accurately deliver precise quantitative amounts of reagents in analytical procedures, especially procedures requiring reagents which when mixed together react with each other or become unstable and lose their potency over a period of time. Of particular importance is that the present invention can be adapted for use in carrying out a wide variety of chemical analyses, not only in the field of clinical chemistry, but in chemical research, water analysis, and chemical process control. The invention is well suited for use in chemical testing of body fluids such as blood, serum, and urine, since in this work a large number of repetitive tests are frequently conducted and these results needed within a short time after the sample is taken. The device, for example, can be adapted for use in carrying out quantitative analyses for many of the blood components which are routinely measured. Thus the device can be adapted for use in the analyses of such blood components as albumin, bilirubin, urea nitrogen, serum glutamicoxalacetic transaminase, chloride, total protein, glucose, uric acid, acid phosphatase and alkaline phosphatase.

In analyzing serum or urine, an aliquot is placed in a specified volume of water and a reagent device is contacted with the mixture, whereupon the binder films containing the reagents dissolve, releasing the reagents into the medium. For example, in one typical analytical procedure for serum glucose sequential reactions can be used. The enzyme glucose oxidase, catalyzes the conversion of glucose to gluconic acid and hydrogen peroxide. The hydrogen peroxide generated can be measured by its reaction with a reducing agent indicator catalyzed by horseradish peroxidase wherein the hydrogen peroxide is converted to water and the reducing agent to a colored pigment. The course of the reaction is observed by noting the increase in absorption of the generated dye. In order to conduct an assay, a reagent containing glucose oxidase, horseradish peroxidase, buffer salts, and reducing agent must be prepared. To this solution an aliquot of a sample containing the analyte is added and the reaction allowed to proceed to termination. In addition to the above reagent, a calibrator or standard glucose solution must also be prepared and utilized in the above assay in order to permit extrapolation of the amount of glucose (analyte) in the sample.

In a typical analytical procedure employing a reagent device of the present invention, an aliquot of the sample containing the analyte is added to an established volume of water. In the analyte solution is immersed one reagent device containing localized reagent-containing polymeric binder elements such that the separate elements dissolve along with their respective reagents and are quantitatively delivered into the medium. The initiated reaction is then allowed to proceed to termination. The reagent device allows the simultaneous delivery of three distinct reagents—buffer salts containing horseradish peroxidase, glucose oxidase, and reducing agent in precise quantitative amounts. For establishing the concentration of glucose in the sample, comparison of the sample assay to an assay conducted with a glucose calibrator reagent device is carried out. In the latter procedure, the reagent device is constructed to deliver four separate reagents simultaneously from four separate elements secured to a single support member—buffer salts containing horseradish peroxidase, glucose oxidase, reducing agent, and a known quantity of glucose, the unknown sample being omitted from the solution. In both procedures the increase in optical density of the oxidized reducing agent can be read in a spectrophotometer.

The present invention can also be adapted for use in carrying out quantitative analysis of water samples from lakes, rivers and industrial fluids. The device can be used in the water analysis of such analytes as aluminum, barium, copper, chloride, iron, bromine, and chlorine. Of special interest is the analysis of chlorine, because the device can be used in the analysis of drinking water or pool water to control the degree of chlorination of these fluids. For example, in the analysis of chlorine, the reagent N,N-diethyl-p-phenylenediamine appropriately buffered can be incorporated in a binder element on a support member so that a specified amount of the reagent can be delivered quantitatively to a specified volume of water containing the analyte. The delivered reagent reacts readily with the free chlorine present in the sample to yield a magenta color whose intensity is related to the amount of free chlorine in the sample. In order to quantitate the level of chlorine in such samples, a calibrator reagent device is employed which is capable of delivering two separate reagents simultaneously, the indicator reagent N,N-diethyl-p-phenylenediamine and calcium hypochlorite to a chlorine free aqueous solution. From the known concentration of chlorine in the calibrator strip and the color intensity of the resulting solution, the concentration of chlorine in the sample can be interpolated.

In still another embodiment, the device of the present invention can be used to conduct immunoassay procedures. In one such immunoassay technique, radioactively labeled compounds are arranged to compete with unlabeled compounds for specific binding sites on an antibody (either insolubilized or capable of insolubilization). The present device can be used to simplify delivery of reagents in such immunoassays. For example, a radioimmunoassay for tetraiodothyronine (T4) can be simplified by incorporating the required reagents individually in separate soluble binder elements on a single support member. The required reagents for the assay consist of standard serum containing T4, radioiodine labeled T4, antibody specific for T4, and precipitating antibody. In addition, a reference graph or standard curve can be generated via the above device by preparing separate devices for each concentration of T4 in the standard serum required to yield a reference graph.

The device in accordance with this invention can be advantageously made so that the type and concentration of binder used in preparing discrete reagent-binder elements on one device can be dissimilar from those on another, one binder dissolving more rapidly than another and allowing the differential release of reactants with time. Similarly, individual reagent-binder elements on a single support member may be made from different binders which dissolve or disperse in water at different rates. In addition, the reagent device can be made in the form of long strips or tapes that are rolled up and inserted in a dispenser. The latter embodiment would likewise allow the automation of reagent delivery by long strips or tapes.

Figure 2:
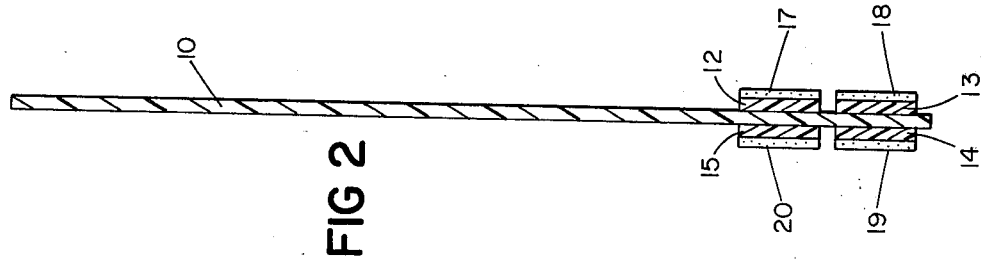
FIG. 2 is a view in section taken along line 2—2 of FIG. 1.
Figure 1:
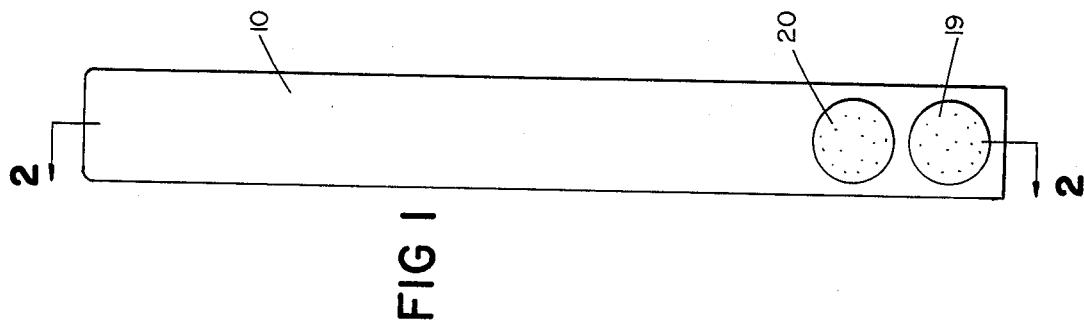
FIG. 1 is a view in front elevation showing one embodiment of the present invention.

As shown in FIGS. 1 and 2, the assay device for delivering precise quantities of reagents comprises a support member 10 in the form of a stiff strip or sheet of water impervious plastic such as polycarbonate to which are cemented four discs 12, 13, 14, 15 of solid water impervious polyester of polystyrene sheet 0.5 cm in diameter. Each disc bears on its outer face an element in the form of a film 17, 18, 19, 20 of dry solid water-soluble binder approximately 0.05 mm thick. In order to improve bonding of the film to its respective disc, the latter may first be treated to render its surface hydrophilic by any conventional procedure, after which the film of binder is formed in place by depositing a solution of the binder on the surface and allowing it to dry. Two or more of films 17-20 carry dispersed within them a precise and known quantity of the desired different reagents, each reagent being dispersed in each film by applying to the surface of the film, by means of a micropipette, a precise and known volume of a water solution of known concentration of the desired reagent, then allowing the film containing the reagent solution to dry. Alternatively, the reagent can be dissolved in an aqueous solution of binder and the mixed solution applied to one of discs 12-15 and dried to form a dry solid film 17-20 containing the reagent dispersed in it.

Figure 3:
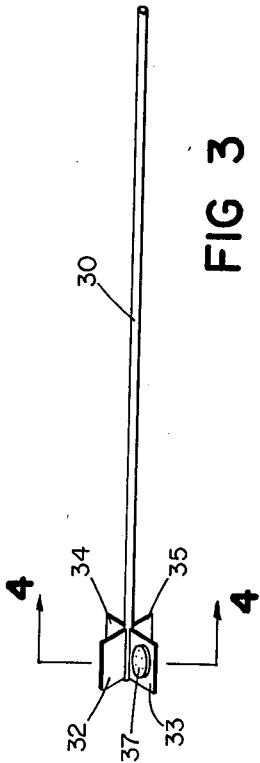
FIG. 3 is an isometric view showing another embodiment of the invention.
Figure 4:
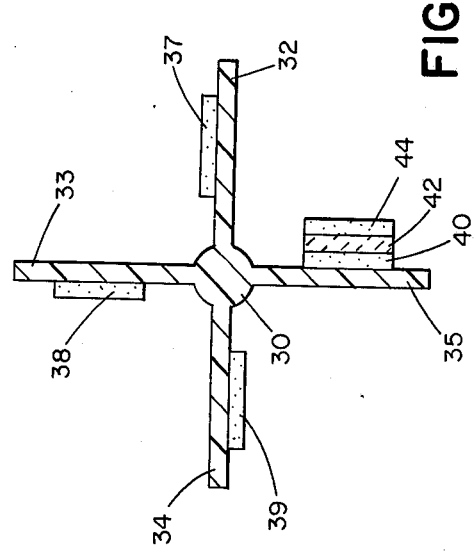
FIG. 4 is a view in section taken along line 4—4 of FIG. 3.

In the embodiment shown in FIGS. 3 and 4, the support member comprises a stiff water impervious rod 30 carrying adjacent its lower end a plurality of projecting fins or propeller blades 32, 33, 34, 35 of stiff water impervious plastic each carrying on one face an element in the form of a dry solid film 37, 38, 39, 40 of water-soluble binder approximately 0.05 mm thick. A desired reagent in precise quantity is dispersed within two or more of films 37-40 by the same procedure as described above for the embodiment of FIGS. 1 and 2. Arranged on the outer surface of reagent-containing film 40 is a dry separator film 42 of the same water-soluble binder free from reagent, serving as a separator or barrier, and on top of film 42 another element in the form of a dry binder film 44 containing a measured quantity of a different water-soluble reagent dispersed in it.

In the embodiments of all of FIGS. 1-4, the upper end of elongated support members 10 and 30 serve as handles while the opposing lower ends carrying the binder films are arranged to be immersed in the aqueous test liquid. The device of FIGS. 3 and 4 can be twirled in the fingers, blades 32-35 serving in that case to stir the liquid.

The following specific examples are intended to illustrate the nature of the invention without acting as a limitation upon its scope.

EXAMPLE 1

A reagent delivery device for the analysis of tetraiodothyronine, such as in body fluids, was prepared in the following manner:

An RIA$^{125}$I-T4 commercially available second-antibody kit for the quantitative determination of T4 was obtained. In order to prepare a device of the present invention containing the reagents in the kit for delivery in an assay procedure the $^{125}$I-T4 second-antibody reagent, (i.e., barbital-bovine serum albumin buffer containing $^{125}$I-T4, ammonium salt of 8-anilino-1-naphthalene sulfonic acid 0.5 mg/ml and the globulin fraction of goat antirabbit gamma globulin), as well as the T4 antiserum reagent (primary antibody), (containing rabbit antiserum to T4 and rabbit gamma globulin), were each concentrated ninefold by "bulb to bulb" lyophilization. The T4 standards, i.e., thyroxine standards of 0, 1, 2, 4, 8, 16 and 32$\mu$ g% in human serum were not concentrated. In each above solution, i.e., T4 standards, concentrated T4 antiserum, and concentrated $^{125}$I-T4 second antibody was dissolved sufficient dextran (m.w. average 70,000) to yield a 20% by weight dextran solution. A volume of 25 microliters of one standard was pipetted onto disc 12 of the device of FIGS. 1 and 2, while 50 $\mu$l of concentrated anti-T4 in 20% dextran was pipetted onto disc 13. Discs 14 and 15 were unneeded for this example. After drying, there remained bonded on disc 12 film 17 consisting of dextran binder in which was dispersed the standard; and on disc 13 was a film 18 consisting of dextran binder in which was dispersed anti-T4. In the same manner, other reagent devices were prepared containing elements having 0, 1, 2, 4, 8, 16 and 32 micrograms percent thyroxine respectively along with a separate element containing anti-T4 serum. The devices so prepared were used by placing each device into 1.0 ml of assay medium prepared by mixing 0.5 ml of barbital buffer containing bovine serum albumin (0.1%) with 0.5 ml $^{125}$I-T4 second antibody buffer. One assay was conducted for each T4 standard. The assay mixture was incubated for 3.5 hours at room temperature, whereupon a precipitate formed. The tubes were centrifuged at 9000 rpm in a Damon IEC HN-S Centrifuge equipped with a fixed head rotor. The individual tubes were decanted of their supernatant and the remaining precipitate counted in a gamma counter. The resulting data were plotted on semi-logarithmic paper to yield a standard curve. A device containing no thyroxine but containing anti-T4 serum prepared as described above could then be contacted with the specimen of the unknown serum to be assayed to which $^{125}$I-T4 second antibody buffer had been added and the results compared with the standard curve.

EXAMPLE 2

Devices were prepared as in Example 1 except that concentrated $^{125}$I-T4 second antibody buffer and T4 standards were placed on the device while barbital buffer and T4 antiserum (primary antibody) were pipetted into 12×75 mm glass tubes. Dextran was employed as the water-soluble binder in each element. A standard curve could be obtained via the same procedure as in Example 1.

Similar results can be obtained by placing all three of the T4 standards, concentrated anti-T4 serum, and concentrated $^{125}$I-T4 second antibody reagent along with dextran binder on separate discs 12, 13 and 14 respectively of the device shown in FIGS. 1 and 2.

EXAMPLE 3

Biuret Test for Protein

A reagent device was prepared as described in Example 1 with the exception that each of the following four reactants was separately applied in an amount of 25 microliters onto discs 12-15 respectively and dried under a stream of warm air to form elements 17-20 respectively.

Reactant 1. To prepare Reactant 1, 44.9 grams sodium potassium tartrate, 0.8 grams sodium hydroxide, 2 grams polyethylene glycol-4000 (to serve as binder) and 14.98 grams copper sulfate were dissolved and diluted to a volume of 100 ml with water.

Reactant 2. Potassium iodide 24.9 grams and 2 grams polyethylene glycol-4000 were dissolved in water to yield a final volume of 100 ml.

Reactant 3. Forty grams of sodium hydroxide and 0.5 grams of polyethylene glycol-4000 were dissolved in water and diluted to 100 ml.

Reactant 4. A solution of 30% Bovine Serum Albumin (BSA) was diluted in 2% polyethylene glycol-4000 containing 0.85% sodium chloride to yield a series of BSA solutions containing 5%, 4%, 3%, 2% and 1% BSA respectively.

To conduct an assay, 1.0 ml of water was added to a 12×75 mm glass test tube and one reagent delivery device per tube was added by immersion. The dissolved reactants were allowed to incubate for 30 minutes at room temperature following which the absorbance at 546 nm was read in a spectrophotometer.

In order to evaluate the performance of the reagent delivery device in the biuret assay for protein, a standard biuret procedure was conducted with the bovine serum albumin standards. (Reinhold, J. G.: Standard Methods of Clinical Chemistry 1:88, 1953). An identical assay response was obtained in the protein concentration range studied by both the assay device of the present invention and the standard biuret procedure.

EXAMPLE 4

The same devices as in Example 3 were prepared except that dextran (m.w. about 70,000) was substituted for the polyethylene glycol-4000 as the solid organic polymeric binder. A similar response to Example 3 was obtained when Dextran T-70 was used as binder in the device.

EXAMPLE 5

Glucose Determination

Reagent devices were prepared as described in Example 3 except that the following four reactants were substituted for those used in Example 3, the polyethylene glycol-4000 in each case serving as the water-soluble binder.

Reactant 1. Five ml of a saturated solution of potassium dihydrogen phosphate adjusted to pH 6.0 with 10 N sodium hydroxide was added to 5.0 ml of 4 M tris hydrochloride adjusted to pH 7.5 with concentrated hydrochloric acid. To the phosphate/tris buffer combination were added 10 mg of horseradish peroxidase whose activity was 82 purpurogallen units per mg of protein. The protein was carefully dissolved by gentle rocking. Polyethylene glycol-4000, 400 mg was added to give a 4% solution.

Reactant 2. A saturated solution of glucose oxidase from a crude extract of *Aspergillus niger* was prepared by gently mixing 1 gram of the lyophilized extract with 5 ml. of water. The resulting solution was filtered to remove insoluble material and 200 mg of polyethylene glycol-4000 added to give a 4% polymer solution.

Reactant 3. O-dianisidine, 40 mg. was dissolved in 10 ml of 0.1 M sodium phosphate buffer pH 3.0 and 400 mg of polyethylene glycol-4000 was added to give a 4% polymer solution.

Reactant 4. Glucose, 11.2 mg was added to 10 ml of water containing 20 mg benzoic acid and 400 mg polyethylene glycol-4000 to yield a standard solution containing 1.12 mg glucose/ml and 4% polymer.

To conduct an assay one assay device was contacted with 1.0 ml of water in a 12×75 mm glass test tube. The reaction was allowed to proceed for 15 minutes and was then terminated with 1.0 ml of 36% sulfuric acid. The absorbance was read at 530 nm after the addition of sulfuric acid. To assay an unknown specimen, an assay device containing reactants 1 to 3 only was prepared and immersed in a 12×75 mm test tube containing 1.0 ml of water and 25 microliters of specimen. The analysis was conducted as with the first reagent device above. The red colored solution was read at 530 nm after termination of the reaction with 36% sulfuric acid. Several devices containing Reagents 1 to 3 were evaluated by using glucose solutions containing 1.12 mg/ml, 0.56 mg/ml, 0.28 mg/ml and 0.14 mg/ml glucose according to the above protocol. In each tube into which a device had been placed a red color developed after the addition of 36% sulfuric acid. The color intensity was read in a spectrophotometer at 530 nm. Results were as follows:

| Concentration of Glucose | Optical Density |
| --- | --- |
| 1.12 mg/ml | 1.075 |
| .56 mg/ml | 0.502 |
| .28 mg/ml | 0.209 |
| .14 mg/ml | 0.102 |
| No glucose | 0.017 |

EXAMPLE 6

Devices as in Example 5 were prepared except that polyvinylpyrrolidone was used as a binder in place of polyethylene glycol-4000. A similar response was obtained when the device was evaluated with a glucose standard.

EXAMPLE 7

Devices as in Example 5 were prepared except that dextran (m.w. average 70,000) was used as a binder film in place of polyethylene glycol-4000. A similar response was obtained when the device was evaluated with a glucose standard.

Similar results are obtained when measured quantities of reactants are dispersed in the films 37–40 of the device illustrated in FIGS. 3 and 4.

EXAMPLE 8

Determination of Total Bilirubin

Reagent devices for detecting and measuring total bilirubin concentrations in biological liquids such as serum were prepared according to the following procedure:

The present invention is utilized with the Jendrassik and Grof method for the determination of total bilirubin in serum or plasma. As conventionally utilized, formation of an azobilirubin complex is effected by reacting bilirubin with diazotized sulfanilic acid prepared in acidic medium by reacting sulfanilic acid with sodium nitrite. Because the diazonium salt is recognized as being unstable, it is necessary to prepare the salt frequently. In the aforementioned procedure, the specimen is added to a solution of diazotized sulfanilic acid followed by a solution of sodium acetate and caffeine-sodium benzoate. The sodium acetate buffers the pH of the diazotization reaction, while the caffeine-sodium benzoate accelerates the coupling of bilirubin with diazotized sulfanilic acid. The diazotization reaction is terminated by the addition of ascorbic acid, which destroys the excess diazo reagent. A strongly alkaline tartrate solution is then added to convert the purple azobilirubin to blue azobilirubin and the intensity of the color is read at 600 nm. The azobilirubin color in the total bilirubin procedure is essentially completely developed in 10 minutes.

A reagent composition and device configuration illustrating the present invention is described below, polyethylene glycol-4000 in each case serving as a water-soluble binder for the reagent:

Reactant 1. To prepare Reactant 1, 1.40 grams of sulfanilic acid, 15.01 grams tartaric acid, and 2 grams polyethylene glycol 4000 were dissolved in water and diluted to a final volume of 100 ml.

Reactant 2. To prepare Reactant 2, 600 mg sodium nitrite, 2 grams polyethylene glycol 4000 and 1 gram mannitol were dissolved in water and diluted to a volume of 100 ml.

Reactant 3. To prepare Reactant 3, 11.35 grams of caffeine, 17.28 grams of sodium benzoate, 28.64 grams of sodium acetate, 2 grams polyvinylpyrrolidone and 0.5 gram polyethylene glycol 4000 were dissolved in water and diluted to a volume of 100 ml.

Reactant 4. To prepare Reactant 4—15.63 grams sodium hydroxide, 54.7 grams sodium potassium tartrate, 2 grams mannitol and 0.1 gram polyvinylpyrrolidone were dissolved in water and diluted to a volume of 100 ml.

Reactant 5. To prepare Reactant 5—12.0 grams L-ascorbic acid, 2 grams polyvinylpyrrolidone, and 0.5 gram polyethylene glycol 4000 were dissolved in water and diluted to a volume of 100 ml.

Four reagent devices were prepared: (A) In the first one, 50 μl of Reactant 1 were pipetted onto disc 12 of the device in FIGS. 1 and 2, while 25 μl of Reactant 2 were pipetted onto disc 13. Discs 14 and 15 were unneeded for this device. The reagents were dried to a film in a stream of warm dry air; (B) In a similar fashion 100 μl of Reactant 3 were pipetted onto a device by pipetting 25 μl of Reactant 3 onto each of discs 12, 13, 14, 15 of the device in FIGS. 1 and 2 and dried to a film; (C) One hundred microliters of Reactant 4 were pipetted onto a device in a similar fashion as described for device 2 above; (D) Another device was prepared by pipetting 25 μl of Reactant 5 onto disc 12 of the device in FIGS. 1 and 2.

To conduct an assay 1.0 ml of water was added to a 12×75 mm glass test tube and reagent delivery device (A) was added. To the dissolved reactants were added 100 μl of sample or standard serum containing bilirubin. Immediately following addition of the sample, reagent delivery device (B) was added and the dissolved reactants allowed to incubate at room temperature for 10 minutes. Following the 10 minute incubation period, device (D) was added to the tube and after dissolution of Reactant 5, device (C) was added. Following dissolution of Reactant 4, the total bilirubin is determined by spectrally measuring the optical density at 600 nm. Samples containing 4.6 mg/dl, 2.3 mg/dl, 1.15 mg/dl, 0.575 mg/dl, 0.288 mg/dl, and 0.00 mg/dl bilirubin when analyzed by the above procedure yielded a blue-green color whose color intensity was proportional to the concentration of bilirubin. When the color intensity (optical density) was read at 600 nm in a spectrophotometer, the results were as follows:

| Concentration Bilirubin | | Color Density |
|---|---|---|
| 4.6 | mg/dl | .463 ± .002 |
| 2.3 | mg/dl | .286 ± .008 |
| 1.15 | mg/dl | .194 ± .004 |
| 0.575 | mg/dl | .143 ± .000 |
| 0.288 | mg/dl | .108 ± .002 |
| 0.000 | mg/dl | .079 ± .011 |

In order to evaluate the performance of the reagent delivery devices in the bilirubin assay, a standard Jendrassik and Grof assay was conducted on the same bilirubin samples. A similar assay response was obtained in the bilirubin concentration range studied by both the assay device of the present invention and the standard method.

Advantages were observed with the devices in that the ascorbic acid reagent in dried form was very stable, whereas solutions of ascorbic acid used in the standard assay had to be prepared fresh daily due to their instability. In addition, the diazo reagent was generated in situ when the reagent device was added to the water sample, whereas this reagent had to be prepared fresh daily when conducting the standard assay.

What is claimed is:

1. A device for precise quantitative introduction of a plurality of reagents into a liquid aqueous assay medium; said device comprising a water-impervious solid support member which is chemically inert to the reagents and to the material to be assayed, secured to one or more faces of said support member two or more discrete and separate elements consisting essentially of carrier solid organic binder which is soluble or dispersible in water, and dispersed in said solid binder a measured quantity of water-soluble or dispersible reagent, the reagent in each said element being reactive with at least one reagent in another element or with at least one constituent in said assay medium, said support member being a stiff elongated member having one portion constructed and arranged as a handle for said device, and having said discrete elements secured to portions thereof removed from said handle, said handle facilitating contact of said discrete elements with liquid assay medium to permit each said reagent and binder to dissolve completely and be mixed in said medium.

2. A device as claimed in claim 1 in which said support member is in the form of a sheet and said elements are secured to opposite faces of said sheet.

3. In the method of assaying a liquid aqueous assay medium by introducing precise quantities of reagents into said medium, the improvement which comprises introducing said reagents by contacting with said medium a device as claimed in claim 2 until each said element has dissolved or dispersed therein.

4. A device as claimed in claim 1 in which two or more of said elements are overlaid in the form of a stack, the bottommost one of which is secured to said support member, and comprising a layer of water-insoluble or water-soluble material interposed as a separator between adjacent elements of said stack.

5. In the method of assaying a liquid aqueous assay medium by introducing precise quantities of reagents into said medium, the improvement which comprises introducing said reagents by contacting with said medium a device as claimed in claim 4.

6. A device as claimed in claim 1 in which one of said elements dissolves in water at a different rate from another.

7. In the method of assaying a liquid aqueous assay medium by introducing precise quantities of reagents into said medium, the improvement which comprises introducing said reagents by contacting with said medium a device as claimed in claim 6.

8. A device as claimed in claim 1 in which said support member is in the form of a sheet and said elements are secured to the same face of said sheet spaced apart from each other.

9. In the method of assaying a liquid aqueous assay medium by introducing precise quantities of reagents into said medium, the improvement which comprises introducing said reagents by contacting with said medium a device as claimed in claim 8.

10. In the method of assaying a liquid aqueous assay medium by introducing precise quantities of reagents into said medium, the improvement which comprises introducing said reagents by contacting with said medium a device as claimed in claim 1 until each said element has dissolved or dispersed therein.

11. The method as claimed in claim 10 including the step of stirring said liquid medium with said support member.

* * * * *